US010952385B2

(12) United States Patent
Haaring et al.

(10) Patent No.: US 10,952,385 B2
(45) Date of Patent: Mar. 23, 2021

(54) QTLS FOR FUSARIUM RESISTANCE IN CUCUMBER

(71) Applicant: RIJK ZWAAN ZAADTEELT EN ZAADHANDEL B.V., De Lier (NL)

(72) Inventors: Cornelis Haaring, De Lier (NL); Apostolos Spyropoulos, De Lier (NL); Magdalena Barbara Lastdrager, De Lier (NL); Lena Johanna Huijbregts-Doorduin, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 15/837,149

(22) Filed: Dec. 11, 2017

(65) Prior Publication Data
US 2018/0103601 A1    Apr. 19, 2018

Related U.S. Application Data

(63) Continuation-in-part of application No. PCT/EP2016/066970, filed on Jul. 15, 2016.

(30) Foreign Application Priority Data

Jul. 27, 2015   (EP) .................................... 15178460

(51) Int. Cl.
*A01H 5/08*       (2018.01)
*C12N 15/82*     (2006.01)
*C12Q 1/6895*   (2018.01)

(52) U.S. Cl.
CPC ............ *A01H 5/08* (2013.01); *C12N 15/8282* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

FOREIGN PATENT DOCUMENTS

| WO | 02/062130 | 8/2002 |
| WO | 2010/098670 | 9/2010 |

OTHER PUBLICATIONS

Rose and Punja Greenhouse Cucumber Cultivars Differ in Susceptibility to Fusarium Root and Stem Rot, HortTechnology 14:240-242 (Year: 2004).*
International Search Report and Written Opinion of the International Searching Authority dated Oct. 4, 2016, which issued during prosecution of International Application No. PCT/EP2016/066970.
Fazio, et al. "Genetic mapping and QTL analysis of horticultural traits in cucumber (*Cucumis sativus* L.) using recombinant inbred lines" Theoretical and Applied Genetics, Jun. 2003, 107(5):864-874.
Rose, et al. "Greenhouse Cucumber Cultivars Differ in Suspectibility to Fusarium Root and Stem Rot" HortTechnology, Apr. 2004, 14(2):240-242.
Zhou, et al. "A Sequencing-Based Linkage Map of Cucumber" Molecular Plant, Jun. 2015, 8:961-963.

* cited by examiner

*Primary Examiner* — Brent T Page
(74) *Attorney, Agent, or Firm* — Duane Morris LLP; Thomas J. Kowalski; Deborah L. Lu

(57) ABSTRACT

The present invention relates to a cucumber plant which carries a QTL1 in its genome that leads to resistance to *Fusarium oxysporum* f. sp. *radicis-cucumerinum*.

15 Claims, 3 Drawing Sheets

Specification includes a Sequence Listing.

Fig. 1

SEQ ID No. 1 - (A) polymorphism SNP on position 65
CTGCAGCCAGCCGCCCTTCTCTTATGTTTTGGCCCCAATACGTTGCGATTCCTCCATGAATGCGGCCAGTAG
TTGGTTCGAAAAAACAGCCTACGAAGCCGAGAATCATGAGAAGAAAGGAAGAAGAAGCGAATGAAGAGA
GTTGAATTTCCATATCGAYCGAAAGTGCAAAGAATGATGTGAGAATCGGTTGGAAGTTGAATATTAA

SEQ ID No. 2 - (A) polymorphism SNP on positions 74 and 75
CTCTATAAATTGATCAATTTAATTAAATTTTGGTGTATGTGCAAAGTCTTCTACGTTGTGCTATATATGTGT
GTTCTTAATTATATATTTTAGATTTGATTGTTATANTTGACACCTTTCATATCTCTAAACCCTAAATCTTATTT
TCATAGAAC

SEQ ID No. 3 - (A) SNP on position 74
CTGCAGGTGAGGTGCAGGTGAAATAGTGCAGAAACCTTGTGAAAATAACCTTTTGCAGCCACCAAATTTGA
TCCAACATACAGTTTGTCCTTTCTCACCATGAAAATAAAATAAACTCTTTAA

SEQ ID No. 4 - (B) SNP on position 120
TTAATGGAGATAAGCCATACTTCAGCGATCAGCACTCTGCCGTGCGGAATATTCCTTTGACTGTTCGAAGG
CCTACATTGAAAGAAGCTCGGCGTATTTATGAACAATTGGTGCAAGTAGTGTATGAAGTAGATGAAGG
AAATATTGTCCACCAGTGAGCACAATGCACTGTTGAGTGCGGCTGCAG

Fig. 2

CS00303 - SEQ ID No. 5 - (A) polymorphism SNP on position 87
TTAATCGGTTCAGGTCAGTGGCAGTGTGTAATTTGCCGGAAGTTGAATGGAAGTGAGGGTGAATACGTGG
CACCGAGCAAAGAAGA<u>T</u>CTTTGTCATTTTCCAGAACTATCATCATCTATGGTTGATTATGTCAGAACTGGGA
ACCGGAGACCAGGATTTATTCCAGCTTCTGACTCRAGAACATCTGCACCTATTGTTCTGGTTATTGACGAGT
CTTTGGATGAGCCACAGCTGCAG

CS00070 - SEQ ID No. 6 - (A) polymorphism SNP on position 39
ACCCCATCGTATACTTTTGCCATCACTTGAAGATATTC<u>A</u>TGGGTATGTCTGCCTACTGATGTAGCATCGATC
GAATGA

CS00300 - SEQ ID NO. 7 - (B) SNP on position 45
CTGCAGCAGAGCACTAAAGAAGGCCAGGATAAATCATAGAACTC<u>T</u>TACCTGACAGATAACTACATCGTCAG
GGCTAGTATTATTGTGCAACTTCTGATGCCATTCTTCCATCATTCCTCCTTTGCAATCATTGTTTCTCTAACA
ACAAATACGTAGTTAA

CS00038 - SEQ ID No. 8 - (B) SNP on position 41
CTCGGCCCAATTAGGAGTCTTCATCGACAGCAAGAAAACC<u>A</u>AACTCACTCGGCCACTTGACTGTCACCTGC
TGCAG

CS00015 - SEQ ID No. 9 - (B) SNP on position 219
ATGGCACAAAAGGCCATAGATATGCTGAAGAGCCTGCCAGACATTTGAAGATAGAAAGGGAAGAGGGTG
AATTATCTCCAAATGGGGATTTTGAAGAAGATAANTTTGCCAATTACGATGGGGAGCTGAAAGCTCTGCCG
AAAGTGAAGGAAGGTGTTGCTGGCAGGCAGTATCCAAGCAACCGAGGCGAGGAAGAATTATGTTGCAGA
GAGGCTGGT<u>A</u>GAGAAAATGATGCTGATGCTGATGACGAAGGGGAGGAAAGTGCACAAAGGTCATCAGAG
GATAGTGAAAATGCCTCGGAGAACGGTGACGTTTCTGCAAGTGATTCCGGTGATGGAGAGGATTGTTCTC
GTGAAGATCATGAGGATGGAGAACATGATGATAACAAGGCTGAGAGTGAAGGTGAGGCAGAAGGGATGG
CCGATGCCCATGATGTAGAAGGAGATGGAACATCTATACCATTCTCTGA

CS00186 - SEQ ID No. 10 - (B) SNP on position 136
CTGCAGCAGAGGCAGAGGAGTCATGGATTGCGTACCTGCAGGGTCAGCTGCCGCACACCAGATATATAGG
CCAAACACTGATGTAATCTGGAAGCAAAATAGATTTAGTGAGCTCTTTCACAATAGAACAAAATG<u>A</u>AAGAC
CACATTCCACAAAAAGATTACAATGATAAAGAACAGGCAGANTGAAGTGACTCAATTCATTTTTCAGATTT
TGGAATTCATTATCAGCACAAGCCCTGTATTTCCGCCTC

Fig. 3

QTL1 - Chromosome 3

| SEQ ID No. | 1 | 3 | 4 | 2 |
|---|---|---|---|---|
| Haplotype QTL1 | A/B | A | B | A/B |
| Haplotype Control | A/B | B | A | A/B |
| SNP | [G/C] | [C/T] | [A/G] | [TC/*] |
| Physical position | 6,996,646 | 7,442,040 | 7,600,352 | 9,480,131 |

QTL2 - Chromosome 5

| SEQ ID No. | 5 | 7 | 8 | 9 | 10 | 6 |
|---|---|---|---|---|---|---|
| Haplotype QTL2 | A/B | B | B | B | B | A/B |
| Haplotype Control | A/B | A | A | A | A | A/B |
| SNP | [T/C] | [G/T] | [G/A] | [G/A] | [G/A] | [A/G] |
| Physical position | 20,877,766 | 21,890,499 | 22,088,673 | 22,292,217 | 22,877,329 | 23,250,404 | of US 10,952,385 B2

SEQUENCE LISTING

```
<160> NUMBER OF SEQ ID NOS: 10

<210> SEQ ID NO 1
<211> LENGTH: 208
<212> TYPE: DNA
<213> ORGANISM: Cucumis sativus
<220> FEATURE:
<221> NAME/KEY: source
<222> LOCATION: 1..208
<223> OTHER INFORMATION: /organism="Cucumis sativus"
      /mol_type="unassigned DNA"

<400> SEQUENCE: 1
ctgcagccag ccgcccttct cttatgtttt ggccccaata cgttgcgatt cctccatgaa      60
tgcggccagt agttggttcg aaaaaacagc ctacgaagcc gagaatcatg agaagaaagg     120
aagaagaagc gaatgaagag agttgaattt ccatatcgay cgaaagtgca aagaatgatg     180
tgagaatcgg ttggaagttg aatattaa                                       208

<210> SEQ ID NO 2
<211> LENGTH: 154
<212> TYPE: DNA
<213> ORGANISM: Cucumis sativus
<220> FEATURE:
<221> NAME/KEY: source
<222> LOCATION: 1..154
<223> OTHER INFORMATION: /organism="Cucumis sativus"
      /mol_type="unassigned DNA"
<220> FEATURE:
<221> NAME/KEY: misc_feature
<222> LOCATION: 107
<223> OTHER INFORMATION: /note="n = a or t or c or g"

<400> SEQUENCE: 2
ctctataaat tgatcaattt aattaaattt tggtgtatgt gcaaagtctt ctacgttgtg      60
ctatatatgt gtgtcttaat tatatatttt agatttgatt gttatanttg acacctttca    120
tatctctaaa ccctaaatct tattttcata gaac                                154

<210> SEQ ID NO 3
<211> LENGTH: 123
<212> TYPE: DNA
<213> ORGANISM: Cucumis sativus
<220> FEATURE:
<221> NAME/KEY: source
<222> LOCATION: 1..123
<223> OTHER INFORMATION: /organism="Cucumis sativus"
      /mol_type="unassigned DNA"

<400> SEQUENCE: 3
ctgcaggtga ggtgcaggtg aaatagtgca gaaaccttgt gaaaataacc ttttgcagcc      60
accaaatttg atccaacata cagtttgtcc tttctcacca tgaaaataaa ataaactctt    120
taa                                                                  123
```

```
<210> SEQ ID NO 4
<211> LENGTH: 189
<212> TYPE: DNA
<213> ORGANISM: Cucumis sativus
<220> FEATURE:
<221> NAME/KEY: source
<222> LOCATION: 1..189
<223> OTHER INFORMATION: /organism="Cucumis sativus"
      /mol_type="unassigned DNA"

<400> SEQUENCE: 4
ttaatggaga taagccatac ttcagcgatc agcactctgc cgtgcggaat attcctttga      60
ctgttcgaag gcctacattg aaagaagctc ggcgtattta tgaacaattg gtgcaagtag     120
tgtatgaagt agatgagaag gaaatattgt ccaccagtga gcacaatgca ctgttgagtg     180
cggctgcag                                                             189

<210> SEQ ID NO 5
<211> LENGTH: 237
<212> TYPE: DNA
<213> ORGANISM: Cucumis sativus
<220> FEATURE:
<221> NAME/KEY: source
<222> LOCATION: 1..237
<223> OTHER INFORMATION: /organism="Cucumis sativus"
      /mol_type="unassigned DNA"

<400> SEQUENCE: 5
ttaatcggtt caggtcagtg gcagtgtgta atttgccgga agttgaatgg aagtgagggt      60
gaatacgtgg caccgagcaa agaagatctt tgtcattttc cagaactatc atcatctatg     120
gttgattatg tcagaactgg gaaccggaga ccaggattta ttccagcttc tgactcraga     180
acatctgcac ctattgttct ggttattgac gagtctttgg atgagccaca gctgcag       237

<210> SEQ ID NO 6
<211> LENGTH: 78
<212> TYPE: DNA
<213> ORGANISM: Cucumis sativus
<220> FEATURE:
<221> NAME/KEY: source
<222> LOCATION: 1..78
<223> OTHER INFORMATION: /organism="Cucumis sativus"
      /mol_type="unassigned DNA"

<400> SEQUENCE: 6
accccatcgt atactttgc catcacttga agatattcat gggtatgtct gcctactgat       60
gtagcatcga tcgaatga                                                    78

<210> SEQ ID NO 7
<211> LENGTH: 160
<212> TYPE: DNA
<213> ORGANISM: Cucumis sativus
<220> FEATURE:
<221> NAME/KEY: source
<222> LOCATION: 1..160
<223> OTHER INFORMATION: /organism="Cucumis sativus"
      /mol_type="unassigned DNA"

<400> SEQUENCE: 7
ctgcagcaga gcactaaaga aggccaggat aaatcataga actcttacct gacagataac      60
tacatcgtca gggctagtat tattgtgcaa cttctgatgc cattcttcca tcattcctcc     120
tttgcaatca ttgtttctct aacaacaaat acgtagttaa                           160
```

```
<210> SEQ ID NO 8
<211> LENGTH: 76
<212> TYPE: DNA
<213> ORGANISM: Cucumis sativus
<220> FEATURE:
<221> NAME/KEY: source
<222> LOCATION: 1..76
<223> OTHER INFORMATION: /organism="Cucumis sativus"
      /mol_type="unassigned DNA"

<400> SEQUENCE: 8
ctcggcccaa ttaggagtct tcatcgacag caagaaaacc aaactcactc ggccacttga     60
ctgtcacctg ctgcag                                                    76

<210> SEQ ID NO 9
<211> LENGTH: 466
<212> TYPE: DNA
<213> ORGANISM: Cucumis sativus
<220> FEATURE:
<221> NAME/KEY: source
<222> LOCATION: 1..466
<223> OTHER INFORMATION: /organism="Cucumis sativus"
      /mol_type="unassigned DNA"
<220> FEATURE:
<221> NAME/KEY: misc_feature
<222> LOCATION: 104
<223> OTHER INFORMATION: /note="n = a or t or c or g"

<400> SEQUENCE: 9
atggcacaaa aggccataga tatgctgaag agcctgccag acatttgaag atagaaaggg     60
aagagggtga attatctcca aatggggatt ttgaagaaga taantttgcc aattacgatg    120
gggagctgaa agctctgccg aaagtgaagg aaggtgttgc tggcaggcag tatccaagca    180
accgaggcga ggaagaatta tgttgcagag aggctggtag agaaaatgat gctgatgctg    240
atgacgaagg ggaggaaagt gcacaaaggt catcagagga tagtgaaaat gcctcggaga    300
acggtgacgt ttctgcaagt gattccggtg atggagagga ttgttctcgt gaagatcatg    360
aggatggaga acatgatgat aacaaggctg agagtgaagg tgaggcagaa gggatggccg    420
atgcccatga tgtagaagga gatggaacat ctataccatt ctctga                  466

<210> SEQ ID NO 10
<211> LENGTH: 251
<212> TYPE: DNA
<213> ORGANISM: Cucumis sativus
<220> FEATURE:
<221> NAME/KEY: source
<222> LOCATION: 1..251
<223> OTHER INFORMATION: /organism="Cucumis sativus"
      /mol_type="unassigned DNA"
<220> FEATURE:
<221> NAME/KEY: misc_feature
<222> LOCATION: 183
<223> OTHER INFORMATION: /note="n = a or t or c or g"

<400> SEQUENCE: 10
ctgcagcaga ggcagaggag tcatggattg cgtacctgca gggtcagctg ccgcacacca     60
gatatatagg ccaaacactg atgtaatctg gaagcaaaat agatttagtg agctctttca    120
caatagaaca aaatgaaaga ccacattcca caaaaagatt acaatgataa agaacaggca    180
gantgaagtg actcaattca tttttcagat tttggaattc attatcagca caagccctgt    240
atttccgcct c                                                        251
```

QTLS FOR FUSARIUM RESISTANCE IN CUCUMBER

RELATED APPLICATIONS AND INCORPORATION BY REFERENCE

This application is a continuation-in-part application of international patent application Serial No. PCT/EP2016/066970 filed Jul. 15, 2016, which published as PCT Publication No. WO 2017/016908 on Feb. 2, 2017, which claims benefit of European patent application Serial No. 15178460.0 filed Jul. 27, 2015.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Dec. 8, 2017, is named 43104_00_2343_SL.txt and is 5,094 bytes in size.

FIELD OF THE INVENTION

The present invention relates to a cucumber plant (*Cucumis sativus* L.) that is resistant to *Fusarium*. The invention further relates to markers linked to the resistance and the use of markers to identify resistant plants. The invention also relates to the seeds and progeny of such plants and to propagation material for obtaining such plants.

BACKGROUND OF THE INVENTION

A large share of cucumber plants is grown in protected cultivation, for example in greenhouses or plastic tunnels. This growing environment can protect the plants from certain environmental conditions, and shield them up to a certain extent from attacks of certain diseases or insects. Especially when the plants are not cultivated in soil but in artificial substrates such as rockwool, the incidence of various soil-borne diseases can be reduced.

One of the diseases however that especially infects cucumber plants grown in a protected environment, both in soil and substrate conditions, is *Fusarium oxysporum* f. sp. *radicis-cucumerinum* (Forc). This soil-borne disease is also known as '*Fusarium* stem and root rot', or '*Fusarium* crown and root rot', and is especially found in greenhouse-grown cucumbers. Young plants are easily infected at a temperature of around 20° C., but often no or limited symptoms will be found at this stage. In many cases symptoms only become visible when plants are grown and bear fruits. The symptoms are mostly expressed as slow wilting, often accompanied by yellowing. Plants that are wilting during the day can initially recover from wilting during cooler nights, but will eventually die. Stem and root rot will often occur as well, which is one of the symptoms that distinguishes this *Fusarium* from the related *Fusarium oxysporum* f sp. *cucumerinum*, usually referred to as '*Fusarium* wilt', which shows only wilting but generally no stem or root rot.

Control of *F. oxysporum* f sp. *radicis-cucumerinum* is rather complex. Prevention by good sanitation measures is a procedure commonly practiced against many pathogens including Forc. Soil or substrate disinfection is a good method to prevent or control soil-borne diseases, but chemical options such as fumigation often negatively affect the environment and are therefore usually not allowed anymore. Non-chemical alternatives that are less damaging are for example heat-treatment or steaming of the soil.

Another commonly used practice for cucumber is the use of resistant rootstocks, usually from crop species that are not affected by Forc, such as an interspecific cross between *Cucurbita maxima* and *Cucurbita moschata*. Although forms of resistance to Forc in cucumber have been identified, no commercial cucumber vegetable varieties having resistance are available yet.

Citation or identification of any document in this application is not an admission that such document is available as prior art to the present invention.

SUMMARY OF THE INVENTION

It is an object of the present invention to provide a cucumber plant (*Cucumis sativus*) with a new resistance to *Fusarium oxysporum* f sp. *radicis-cucumerinum*.

It is an object of the present invention to provide a cucumber plant (*Cucumis sativus*) that carries a genetic determinant which leads to resistance to *Fusarium oxysporum* f sp. *radicis-cucumerinum*.

It is an object of the present invention to provide molecular markers to identify plants carrying the genetic determinant of the invention.

During the research that led to the present invention a genetic determinant, in particular a QTL, was identified that, when present in a cucumber plant, results in resistance to *Fusarium oxysporum* f. sp. *radicis-cucumerinum*.

The invention thus relates to a cucumber plant which carries a QTL that leads to resistance to *Fusarium oxysporum* f. sp. *radicis-cucumerinum*.

Said QTL1 is located on chromosome 3 between marker sequences SEQ ID No. 1 and SEQ ID No. 2 and can be identified by any of the markers having SEQ ID No. 3, and/or SEQ ID No. 4. QTL1 may be as comprised in the genome of a cucumber plant representative seed of which was deposited with the NCIMB under deposit numbers NCIMB 42438 and NCIMB 42439.

Optionally, in addition to the QTL1 also a QTL2 is present, which is located on chromosome 5 between marker sequences SEQ ID No. 5 and SEQ ID No. 6 and which can be identified by any of the markers on chromosome 5 having SEQ ID No. 7, SEQ ID No. 8, SEQ ID No. 9, and/or SEQ ID No. 10, or any combination of these SEQ ID Nos. QTL2 may be as comprised in the genome of a cucumber plant representative seed of which was deposited with the NCIMB under deposit number NCIMB 42439. A cucumber plant of the invention may comprise both QTLs, each either in homozygous or heterozygous form. The invention further relates to progeny of the plant, propagation material for the plant and to markers for identifying the QTLs and their use. In one embodiment the invention relates to a cucumber plant which carries a QTL1 that leads to resistance to *Fusarium* oxysporum f sp. radicis-cucumerinum, which QTL1 is located on chromosome 3 between marker sequences SEQ ID No. 1 and SEQ ID No. 2.

In one embodiment the presence of QTL1 that leads to resistance to *Fusarium oxysporum* f sp. *radicis-cucumerinum* can be identified by a marker on chromosome 3 having SEQ ID No. 3 and/or SEQ ID No. 4. In a particular embodiment, QTL1 is linked to any of the markers on chromosome 3 having SEQ ID No. 3 and/or SEQ ID No. 4, or to the combination of these markers.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

Deposits

Seeds of cucumber *Cucumis sativus* EX 5.008 that comprise QTL1 in homozygous form and seeds of cucumber *Cucumis sativus* EX 5.009 that comprise QTL1 and QTL2 in heterozygous form were deposited with NCIMB Ltd, Ferguson Building, Craibstone Estate, Bucksburn, Aberdeen AB21 9YA, UK on 21 Jul. 2015 under deposit accession number NCIMB 42438 and NCIMB 42439 respectively.

The Deposits with NCIMB Ltd, under deposit accession number NCIMB 42438 and NCIMB 42439 were made pursuant to the terms of the Budapest Treaty. Upon issuance of a patent, all restrictions upon the deposit will be removed, and the deposit is intended to meet the requirements of 37 CFR § § 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The following detailed description, given by way of example, but not intended to limit the invention solely to the specific embodiments described, may best be understood in conjunction with the accompanying drawings.

FIG. 1: SNP marker sequences of SEQ ID Nos. 1-4 related to QTL1, chromosome 3. Behind the SEQ ID No. it is indicated if version A or B of the sequence is given. The version given is the version that is related to the QTL1 of the invention, except for SEQ ID Nos. 1 and 2 for which both versions can be used for positioning the QTL1 region (see also FIG. 3). Also the position of the polymorphism or the SNP is mentioned, and the nucleotide at that position is bold. Using FIG. 3, the haplotypes for standard cucumber/control plants as compared to the QTL region of plants of the invention can be determined.

FIG. 2: SNP marker sequences of SEQ ID Nos. 5-10 related to QTL2, chromosome 5. See explanation at FIG. 1 for further description. For positioning the QTL2 region both versions of SEQ ID Nos. 5 and 6 can be used.

FIG. 3: Haplotypes of the SNP markers for QTL1 and QTL2. The haplotype indicates which combination of versions of the markers is indicative for the QTL. The nucleotide change is indicated as [X/Y], whereby X is version A and Y is version B. For SEQ ID No. 2, version B has a deletion of 2 nucleotides, [TC], whereby the first nucleotide corresponds to the indicated physical position of the public cucumber genome. Also the physical position of the SNP corresponding to the public cucumber genome based on variety Chinese Long 9930 is indicated in this Figure.

DETAILED DESCRIPTION OF THE INVENTION

The research that led to the present invention had as aim to identify and characterize new sources of resistance to *Fusarium oxysporum* f. sp. *radicis-cucumerinum* that could be conveniently used in cucumber varieties that are commercially interesting for high-end protected cultivation. When a resistance inherits in a recessive way, both parents of a hybrid variety need to have the resistance for it to be expressed in the F1. For a breeding programme this means that the resistance needs to be introgressed in all the material for a certain market in which the disease is prevalent. It is therefore advantageous if the resistance is inherited as a dominant, incompletely dominant, or intermediately inherited trait.

During the execution of the breeding activities a new resistance to *Fusarium oxysporum* f. sp. *radicis-cucumerinum* however was identified and introgressed in breeding lines having the capacity to be used for high-end commercial varieties. This material has a good level of resistance under disease pressures that were tested, and does not show a recessive type of inheritance. This means that a cross between two parents of which only one shows a high level of resistance will result in an F1 that still has a certain level of resistance. The best results however are obtained when both parents have the resistance and the genetic determinant for the resistance is homozygously present. The inheritance of the resistance can therefore be called intermediate or incompletely dominant.

A QTL mapping study was performed to identify the genetic region for the cause of this trait. In this study a QTL, designated QTL1, was identified on chromosome 3, between the positions that can be identified with marker sequences SEQ ID No. 1 and SEQ ID No. 2. When these markers are positioned on the publicly available genome sequence for *Cucumis sativus* based on the cucumber variety Chinese Long 9930, the indicated SNP, a [G/C] polymorphism, in SEQ ID No. 1 corresponds to physical position 6,996,646 bp and the indicated polymorphism [TC/*] in SEQ ID No. 2 corresponds to physical positions 9,480,131 and 9,480,132 bp. The location of the QTL1 is therefore also derivable from this public map and is relative to said physical positions. The cucumber genome sequence based on Chinese Long 9930 can be accessed at: http://www.icugi.org/cgi-bin/gb2/gbrowse/cucumber_v2/, which is the reference for 'the public cucumber genome' as used herein.

Further genotyping resulted in the mapping of various SNP markers that can be used for identification of QTL1, which SNP markers are represented by SEQ ID Nos. 3 and 4. The sequences of SEQ ID Nos. 1-4 related to QTL1 can be found in FIG. 1.

On position 65 of SEQ ID No. 1 a 'G' is present, but alternatively a 'C' can be present, resulting in a possible [G/C] polymorphism on position 65; on positions 74 and 75 of SEQ ID No. 2 'TC' is present, but these can alternatively be deleted, resulting in a possible [TC/*] polymorphism on positions 74 and 75, whereby '*' means that 'TC' is deleted. From both SEQ ID Nos. both versions can be used to identify the position of the QTL1 region.

On position 74 of SEQ ID No. 3 a 'C' is present as a SNP from the alternative 'T', whereby the presence of 'C' is indicative for the presence of QTL1; on position 120 of SEQ ID No. 4 an 'G' is present, as a SNP from the alternative 'A', whereby the presence of 'G' is indicative for the presence of QTL1 (FIG. 3).

In the QTL mapping study also a second QTL was identified, designated QTL2. This QTL is located on chromosome 5, between marker sequences SEQ ID No. 5 and SEQ ID No. 6. When these markers are positioned on the publicly available genome sequence for *Cucumis sativus* based on the cucumber variety Chinese Long 9930, the indicated SNP, a [T/C] polymorphism, in SEQ ID No. 5 corresponds to physical position 20,877,766 bp and the indicated SNP, a [A/G] polymorphism, in SEQ ID No. 6 corresponds to physical position 23,250,404 bp. The location of the QTL2 is therefore also derivable from this public map and is relative to said physical positions.

In one embodiment the invention relates to a cucumber plant which carries QTL1 and optionally QTL2 that leads to resistance to *Fusarium oxysporum* f. sp. *radicis-cucumerinum*, which QTL2 is positioned on chromosome 5 between marker sequences SEQ ID No. 5 and SEQ ID No. 6.

Further genotyping of QTL2 led to the mapping of various SNP markers that can be used for the identification of QTL2, which SNP markers are represented by SEQ ID Nos. 7-10. The sequences of SEQ ID Nos. 5-10 related to QTL2 can be found in FIG. 2.

On position 87 of SEQ ID No. 5 a 'T' is present, but alternatively a 'C' can be present, resulting in a possible [T/C] polymorphism on position 87; on position 39 of SEQ ID No. 6 an 'A' is present, but alternatively a 'G' can be present, resulting in a possible [A/G] polymorphism on position 39. From both SEQ ID Nos. both versions can be used to identify the position of the QTL2 region.

On position 45 of SEQ ID No. 7 a 'T' is present as a SNP from the alternative 'G', whereby the presence of 'T' is indicative for the presence of QTL2; on position 41 of SEQ ID No. 8 a 'A' is present as a SNP from the alternative 'G', whereby the presence of 'A' is indicative for the presence of QTL2; on position 219 of SEQ ID No. 9 a 'A' is present as a SNP from the alternative 'G', whereby the presence of 'A' is indicative for the presence of QTL2; on position 136 of SEQ ID No. 10 a 'A' is present as a SNP from the alternative 'G', whereby the presence of 'A' is indicative for the presence of QTL2 (FIG. 3).

In one embodiment the presence of QTL2 that leads to resistance to *Fusarium oxysporum* f. sp. *radicis-cucumerinum* can be identified by any of the markers on chromosome 5 having SEQ ID No. 7, SEQ ID No. 8, SEQ ID No. 9, and/or SEQ ID No. 10, or any combination of these SEQ ID Nos. In a particular embodiment, QTL2 is linked to any of the markers on chromosome 5 having SEQ ID No. 7, SEQ ID No. 8, SEQ ID No. 9, and/or SEQ ID No. 10, or to any combination of these markers.

In one embodiment, the invention relates to a cucumber plant which may comprise a QTL1 that leads to resistance to *Fusarium oxysporum* f. sp. *radicis-cucumerinum*, which QTL1 may be as comprised in a cucumber plant representative seed of which was deposited with the NCIMB under deposit numbers NCIMB 42438 and NCIMB 42439. Such a plant of the invention therefore has the same QTL1 as the QTL1 that is present in deposit NCIMB 42438 and/or in deposit NCIMB 42439.

In one embodiment, the QTL1 that leads to resistance to *Fusarium oxysporum* f. sp. *radicis-cucumerinum* is introgressed from a cucumber plant which may comprise said QTL1, representative seed of which was deposited with the NCIMB under deposit numbers NCIMB 42438 and NCIMB 42439.

In one embodiment, the QTL1 may be as comprised in NCIMB 42438 and/or NCIMB 42439 is located on chromosome 3 between marker sequences SEQ ID No. 1 and SEQ ID No. 2.

In one embodiment, QTL1 may be as comprised in NCIMB 42438 and/or NCIMB 42439 is linked to any of the markers SEQ ID No. 3 and/or SEQ ID No. 4.

In one embodiment, the invention relates to a cucumber plant which may comprise a QTL2 that leads to resistance to *Fusarium oxysporum* f. sp. *radicis-cucumerinum* in addition to QTL1, which QTL2 may be as comprised in a cucumber plant representative seed of which was deposited with the NCIMB under deposit number NCIMB 42439. Such a plant of the invention therefore has the same QTL2 as the QTL2 that is present in deposit NCIMB 42439.

In one embodiment the QTL2 that leads to resistance to *Fusarium oxysporum* f. sp. *radicis-cucumerinum* is introgressed from a cucumber plant which may comprise said QTL2, representative seed of which was deposited with the NCIMB under deposit number NCIMB 42439.

In one embodiment the QTL2 may be as comprised in NCIMB 42439 is located on chromosome 5 between marker sequences SEQ ID No. 5 and SEQ ID No. 6.

In one embodiment the QTL2 may be as comprised in NCIMB 42439 is linked to any of the markers on chromosome 5 having SEQ ID No. 7, SEQ ID No. 8, SEQ ID No. 9, and/or SEQ ID No. 10, or any combination of these SEQ ID Nos.

In deposit NCIMB 42438 and/or NCIMB 42439 QTL1 is linked to at least one of the markers having SEQ ID No. 3 or SEQ ID No. 4, or to the combination thereof.

In deposit NCIMB 42439 QTL2 is linked to at least one of the markers having SEQ ID No. 7, SEQ ID No. 8, SEQ ID No. 9, and/or SEQ ID No. 10, or to a combination thereof.

Resistance to *Fusarium oxysporum* f. sp. *radicis-cucumerinum* (Forc) of this invention is a resistance that is expressed when QTL1 and optionally QTL2 of the invention is present heterozygously or homozygously. When the QTL is present homozygously, the level of the resistance is higher. In a particular embodiment the level of resistance is higher when QTL1 is homozygously present.

The phenotypic presence of the resistance can be tested using a bio-assay. Symptoms of Forc can be expressed in different ways, and therefore various aspects of the disease can be observed. A bio-assay to determine the resistance of the invention is preferably done on young plants. The optimum temperature for this bio-assay is between 21° C. and 25° C.; a possible temperature regime is 25° C. by day and night. Six or seven days after the plants are sown, when they are in the cotyledon stage, they are inoculated. About one week (6 or 7 days) after inoculation the first observation should be done. Table 1 gives an overview of the features that can be observed to determine the presence of resistance as compared to a susceptible cucumber plant.

TABLE 1 features to determine Forc resistance

| | cotyledon | | hypocotyl rot |
|---|---|---|---|
| 0 | no symptoms | 0 | no |
| 1 | some yellowing | 1 | yes |
| 2 | moderate to heavy yellowing | | |
| 3 | dead plant | | |

| | leaves | | wilting |
|---|---|---|---|
| 0 | no symptoms | 0 | no |
| 1 | some yellowing | 1 | yes (whole plant) |
| 2 | moderate to heavy yellowing | | |
| 3 | dead plant | | |

To get to a reliable observation, a minimum of 18 plants per observed accession should be used, which are divided over a minimum of two repetitions. The first observation is done about one week after inoculation, optionally again 3-4 days later, again 3-4 days later, and at least one more time after 6-7 days. In total thus at least three, preferably four, observations are made over a period of two weeks, which is until about 3 weeks after inoculation, but the observation period can also be extended depending on the severity of the test.

Plants that are susceptible to Forc already show clear symptoms for all features at 10 days after inoculation, whereby the majority of the plants has hypocotyl rot (score 1) and is wilted (score 1). Two weeks after inoculation at least 80% of susceptible plants scores in the highest category (i.e. a score of '3' for cotyledon or leaves, or a score of '1' for hypocotyl rot or wilting), and at three weeks after inoculation at least 90%, but usually 100%, of susceptible plants scores in the highest category. This is also a check to determine that the bio-assay has been carried out correctly. As a susceptible control for example the variety Ventura F1 or variety Kaspian F1 can be used.

A cucumber line that has the resistance of the present invention can show some to moderate yellowing (score 1 or 2) of the cotyledons at 10 days after inoculation, but at least 80% of the plants does not show any symptoms yet for the other features, i.e. for leaf yellowing, hypocotyl rot, and wilting they still score 0. At two weeks after inoculation a clear difference in symptom severity can be observed when compared to a susceptible control, whereby the majority of the resistant plants has a score 0 for hypocotyl rot or wilting.

Cucumber material that is a cross between a susceptible and a resistant parent in general performs comparable to the resistant parent for most features at 10 days after inoculation. For wilting, but depending on the bio-assay conditions also for other features, plants of the cross can show more wilting than the resistant parent at this stage, so more plants will have a score of 1 for this feature, however it will be less than the susceptible parent. The same is true at two weeks after inoculation, whereby especially for the features hypocotyl rot and wilting the plants of the cross tend to show more symptoms, so more plants have a score 1 for these features, than the plants of the resistant parent. This cucumber material that shows an intermediate level of the resistance is also a part of the invention.

Example 1 describes more in detail a bio-assay that can be used for determining the Forc resistance of the present invention. It has to be realized that the results of bio-assays are strongly influenced by aspects such as environmental factors and inoculum conditions, that cannot always be exactly reproduced, and the scores as presented can therefore not be regarded as absolute figures. Hence it is essential that a sufficiently large number of plants is included in an observation, and a proper susceptible control is used for comparison. From the figures presented in Example 1 it can be observed that, as is typical for Forc, some plants do show wilting in an earlier stage but temporary recover at a later observation date.

The QTL1 and QTL2 of the present invention that lead to resistance to *Fusarium oxysporum* f. sp. *radicis-cucumerinum* in cucumber, do not appear to contribute to resistance to *Fusarium oxysporum* f. sp. *cucumerinum* (Foc).

Introgression of a QTL as used herein means introduction of a QTL from a donor plant which may comprise said QTL into a recipient plant not carrying said QTL by standard breeding techniques, wherein selection can be done phenotypically by means of observation of the resistance to *Fusarium oxysporum* f. sp. *radicis-cucumerinum*, or selection can be done with the use of markers through marker assisted breeding, or combinations of these. Selection is started in the F1 or any further generation from a cross between the recipient plant and the donor plant, suitably by using markers as identified herein. The skilled person is however familiar with creating and using new molecular markers that can identify or are linked to the trait of resistance to *Fusarium oxysporum* f. sp. *radicis-cucumerinum*. Development and use of such markers for identification and selection of plants of the invention is also part of the invention.

In one embodiment a cucumber plant of the invention may comprise a combination of QTL1 and QTL2. In one embodiment the invention relates to a cucumber plant which may comprise QTL1 and QTL2 as defined herein, the presence of which QTL1 and QTL2 in the genome of a cucumber plant leads to resistance to *Fusarium oxysporum* f. sp. *radicis-cucumerinum*.

In one embodiment a cucumber plant of the invention with resistance to *Fusarium oxysporum* f sp. *radicis-cucumerinum* may comprise QTL1 and optionally QTL2 in homozygous form. In one embodiment a cucumber plant of the invention with resistance to *Fusarium oxysporum* f sp. *radicis-cucumerinum* may comprise QTL1 in homozygous form and QTL2 in heterozygous form, or may comprise QTL1 in heterozygous form and QTL2 in homozygous form, or may comprise both QTL1 and QTL2 in heterozygous form.

The invention also relates to a cucumber fruit or a cucumber plant carrying only one allele of QTL1 or QTL2, which plant or fruit can be used as a source for the development of a plant of the invention which may comprise at least two alleles of at least one of QTL1 and QTL2.

The term "an allele of QTL1 and/or QTL2" as used herein is the version of the QTL that leads to resistance to *Fusarium oxysporum* f. sp. *radicis-cucumerinum*. The wild type allele does not lead to resistance. The presence of an allele of QTL1 or QTL2 can suitably be identified using a marker as described herein. The presence of at least two alleles for example means that QTL1 can be present homozygously, or QTL2 can be present homozygously, or both QTLs can be present heterozygously. Optionally one or two additional alleles can be present in a plant of the invention that has resistance to *Fusarium oxysporum* f sp. *radicis-cucumerinum*. In a preferred embodiment at least QTL1 is present in homozygous form.

In deposit number NCIMB 42438 QTL1 is present in homozygous form. In deposit number NCIMB 42439 QTL1 and QTL2 are both present in heterozygous form.

The invention also relates to the use of a plant of the invention that may comprise QTL1 and optionally QTL2 as a source of propagating material.

The invention also relates to the use of a plant of the invention that may comprise QTL1 and optionally QTL2 in plant breeding.

The invention furthermore relates to a cell of a plant as claimed. Such cell may be either in isolated form or may be part of the complete plant or parts thereof and then still constitutes a cell of the invention because such a cell harbours the genetic information that leads to resistance to *Fusarium oxysporum* f. sp. *radicis-cucumerinum* of a cucumber plant. Each cell of a plant of the invention carries the genetic information that leads to resistance to *Fusarium oxysporum* f. sp. *radicis-cucumerinum*. Such a cell of the invention may also be a regenerable cell that can be used to regenerate a new plant of the invention. The presence of genetic information as used herein is the presence of QTL1 and optionally QTL2 as defined herein.

The invention also relates to tissue of a plant as claimed. The tissue can be undifferentiated tissue or already differentiated tissue. Undifferentiated tissues are for example stem tips, anthers, petals, pollen, and can be used in micropropagation to obtain new plantlets that are grown into new plants of the invention. The tissue can also be grown from a cell of the invention.

The invention according to a further aspect thereof relates to seed, wherein the plant that can be grown from the seed is a plant of the invention, which may comprise QTL1 and optionally QTL2 which leads to resistance to *Fusarium oxysporum* f. sp. *radicis-cucumerinum* in a cucumber plant. The invention also relates to seeds of a plant as claimed. The seeds harbour the QTL1 and optionally QTL2 that, when a plant is grown from the seeds, makes this plant a plant of the invention.

The invention also relates to progeny of the plants, cells, tissues and seeds of the invention, which progeny may comprise QTL1 and optionally QTL2 that leads to resistance to *Fusarium oxysporum* f sp. *radicis-cucumerinum*. Such progeny can in itself be plants, cells, tissues, or seeds.

As used herein the word 'progeny' is intended to mean the first and all further descendants from a cross with a plant of the invention that may comprise QTL1 and optionally QTL2 that leads to resistance to *Fusarium oxysporum* f sp. *radicis-cucumerinum*.

'Progeny' also encompasses plants that carry QTL1 and/or QTL2 of the invention and have the trait of the invention, and are obtained from other plants or progeny of plants of the invention by vegetative propagation or multiplication. Progeny of the invention suitably may comprise QTL1 and/or QTL2 and resistance to *Fusarium oxysporum* f. sp. *radicis-cucumerinum*.

The term "trait of the invention" as used herein is intended to refer to the trait of having resistance to *Fusarium oxysporum* f. sp. *radicis-cucumerinum*. The trait does not comprise resistance against *Fusarium oxysporum* f. sp. *cucumerinum* (Foc).

The invention further relates to parts of a claimed plant that are suitable for sexual reproduction. Such parts are for example selected from the group consisting of microspores, pollen, ovaries, ovules, embryo sacs, and egg cells. In addition, the invention relates to parts of a claimed plant that are suitable for vegetative reproduction, which are in particular cuttings, roots, stems, cells, protoplasts. The parts of the plants as mentioned above are considered propagation material. The plant that is produced from the propagation material may comprise QTL1 and optionally QTL2 that leads to resistance to *Fusarium oxysporum* f sp. *radicis-cucumerinum*.

According to a further aspect thereof the invention provides a tissue culture of a plant carrying the QTL1 and optionally QTL2 of the invention, which is also propagation material. The tissue culture may comprise regenerable cells. Such tissue culture may be selected or derived from any part of the plant, in particular from leaves, pollen, embryos, cotyledon, hypocotyls, meristematic cells, roots, root tips, anthers, flowers, seeds, and stems. The tissue culture can be regenerated into a plant carrying the QTL1 and optionally QTL2 of the invention, which regenerated plant expresses the trait of the invention and is also part of the invention.

The invention furthermore relates to hybrid seed and to a method for producing such hybrid seed which may comprise crossing a first parent plant with a second parent plant and harvesting the resultant hybrid seed, wherein said first parent plant and/or said second parent plant has the QTL1 and optionally QTL2 of the invention. The resulting hybrid plant that may comprise the QTL1 and optionally QTL2 of the invention and which shows resistance to *Fusarium oxysporum* f. sp. *radicis-cucumerinum* is also a plant of the invention.

In one embodiment the plant of the invention which may comprise the QTL1 and/or QTL2 of the invention either homozygously or heterozygously is a plant of an inbred line, a hybrid variety, a doubled haploid, or a plant of a segregating population. A hybrid variety is a hybrid that is a cross between two inbred lines as parents. Suitably, a parent plant is a plant of an inbred line.

The invention also relates to a method for the production of a cucumber plant having the QTL1 and optionally QTL2 that leads to resistance to *Fusarium oxysporum* f sp. *radicis-cucumerinum* by using a seed that may comprise QTL1 and optionally QTL2 for growing the said cucumber plant. The seeds are suitably seeds of which a representative sample was deposited with the NCIMB under deposit numbers 42438 or 42439.

In one embodiment, the invention relates to cucumber plants of the invention that carry the QTL1 and optionally QTL2 of the invention which leads to resistance to *Fusarium oxysporum* f. sp. *radicis-cucumerinum*, and that have acquired said QTL1 and/or QTL2 from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

In one embodiment, the source from which the QTL1 and/or QTL2 of the invention is acquired is formed by plants grown from seeds of which a representative sample was deposited under accession number NCIMB 42438 or NCIMB 42439, or from the deposited seeds NCIMB 42438 and/or NCIMB 42439, or from sexual or vegetative descendants thereof, or from another source which may comprise the QTL1 and/or QTL2 as defined herein that leads to the resistance to *Fusarium oxysporum* f. sp. *radicis-cucumerinum* of the invention, or from a combination of these sources.

In a preferred embodiment, the invention relates to non-transgenic *Cucumis sativus* plants. The source for acquiring the QTL1 and/or QTL2 of the invention, to obtain a plant of the invention that has resistance to *Fusarium oxysporum* f. sp. *radicis-cucumerinum*, is suitably a *Cucumis sativus* plant that carries the QTL1 may be as comprised homozygously in NCIMB 42438 or may be as comprised heterozygously in NCIMB 42439, or the QTL2 may be as comprised heterozygously in NCIMB 42439, or alternatively a plant of a *Cucumis* species that carries one or both of said QTLs and that can be crossed with *Cucumis sativus*. When a *Cucumis* species other than *Cucumis sativus* is used as the source of a QTL of the invention, optionally, techniques such as embryo rescue, backcrossing, or other techniques known to the skilled person can be performed to obtain seeds of the interspecific cross, which seeds can be used as the source for further development of a non-transgenic *Cucumis sativus* plant that shows resistance to *Fusarium oxysporum* f. sp. *radicis-cucumerinum*.

To obtain a QTL from a source in which it is heterozygously present, seeds of such plant can be grown and flowers can be pollinated with pollen from the same plant or from a plant that also has the QTL heterozygously to obtain fruits with seeds. When these seeds are sown, the resulting plants will segregate according to normal segregation ratios, which means that about 25% of the plants will have the QTL homozygously, about 50% will have the QTL heterozygously, and about 25% will not have the QTL. The presence of the QTL for selection of a preferred plant, having the QTL either homozygously or heterozygously, can suitably be determined using the markers as described herein. Alternatively, plants can be phenotypically observed and visually selected for the presence of resistance to *Fusarium oxysporum* f sp. *radicis-cucumerinum*. The skilled person is aware of how to combine QTLs in heterozygous and homozygous form using known breeding and selection procedures.

The invention also relates to the germplasm of plants of the invention. The germplasm is constituted by all inherited characteristics of an organism and according to the invention encompasses at least the trait of the invention. The germplasm can be used in a breeding programme for the development of cucumber plants having resistance to *Fusarium oxysporum* f sp. *radicis-cucumerinum*. The use of the germplasm that may comprise QTL1 and/or QTL2 leading to resistance to *Fusarium oxysporum* f. sp. *radicis-cucumerinum* in breeding is also part of the present invention.

The invention also concerns the use of QTL1 and/or QTL2 leading to the trait of the invention for the development of cucumber plants that have resistance to *Fusarium oxysporum* f sp. *radicis-cucumerinum*.

As used herein, a marker is genetically 'linked to' a QTL and can be used for identification of that QTL when the recombination between marker and QTL, i.e. between marker and trait, is less than 5% in a segregating population resulting from a cross between a plant which may comprise the QTL and a plant lacking the QTL.

In one embodiment the invention relates to a marker for identification of QTL1 which leads to resistance to *Fusarium oxysporum* f. sp. *radicis-cucumerinum*, which marker is selected from the group of SEQ ID No. 1, SEQ ID No. 2, SEQ ID No. 3, and SEQ ID No. 4. In one embodiment the invention relates to a marker for identification of QTL2 which leads to resistance to *Fusarium oxysporum* f. sp. *radicis-cucumerinum*, which marker is selected from the group of SEQ ID No. 5, SEQ ID No. 6, SEQ ID No. 7, SEQ ID No. 8, SEQ ID No. 9, and SEQ ID No. 10. In a preferred embodiment, the markers for identification are markers of SEQ ID No. 3, and/or SEQ ID No. 4 for QTL1 and markers of SEQ ID No. 7, SEQ ID No. 8, SEQ ID No. 9, and/or SEQ ID No. 10 for QTL2. All markers can be used to develop other markers for the QTLs.

In one embodiment, the invention relates to the use of a marker for identification of QTL1 which leads to resistance to *Fusarium oxysporum* f. sp. *radicis-cucumerinum*, which marker is selected from the group of SEQ ID No. 1, SEQ ID No. 2, SEQ ID No. 3, and SEQ ID No. 4. In one embodiment the invention relates to the use of a marker for identification of QTL2 which leads to resistance to *Fusarium oxysporum* f. sp. *radicis-cucumerinum*, which marker is selected from the group of SEQ ID No. 5, SEQ ID No. 6, SEQ ID No. 7, SEQ ID No. 8, SEQ ID No. 9, and SEQ ID No. 10. In a preferred embodiment, the markers of SEQ ID No. 3, and/or SEQ ID No. 4 are used for identification of QTL1 and the markers of SEQ ID No. 7, SEQ ID No. 8, SEQ ID No. 9, and/or SEQ ID No. 10 are used for identification of QTL2.

In one aspect the invention relates to a method for production of a cucumber plant that has resistance to *Fusarium oxysporum* f. sp. *radicis-cucumerinum*, which may comprise QTL1 and optionally QTL2 that leads to resistance to *Fusarium oxysporum* f sp. *radicis-cucumerinum*, which may comprise:
  (a) crossing a plant comprising QTL1 and/or QTL2, representative seed of which plant was deposited as NCIMB 42438 and/or NCIMB 42439, with a plant not comprising the same QTL, to obtain an F1 population;
  (b) optionally performing one or more rounds of selfing and/or crossing a plant from the F1 to obtain a further generation population;
  (c) selecting a plant that may comprise QTL1 and optionally QTL2 and has resistance to *Fusarium oxysporum* f. sp. *radicis-cucumerinum*, suitably by using molecular markers linked to one or both of the desired QTLs. The plant can also be phenotypically selected for having resistance to *Fusarium oxysporum* f. sp. *radicis-cucumerinum*.

The invention additionally provides a method of introducing another desired trait into a cucumber plant which may comprise resistance to *Fusarium oxysporum* f. sp. *radicis-cucumerinum*, which may comprise:
  (a) crossing a cucumber plant which may comprise QTL1 and optionally QTL2 that leads to resistance to *Fusarium oxysporum* f. sp. *radicis-cucumerinum*, representative seed of which was deposited with the NCIMB as NCIMB 42438 and/or NCIMB 42439, with a second cucumber plant that may comprise the other desired trait to produce F1 progeny;
  (b) selecting an F1 progeny that may comprise QTL1 and optionally QTL2 for resistance to *Fusarium oxysporum* f sp. *radicis-cucumerinum* and may comprise the other desired trait;
  (c) crossing the selected F1 progeny with either parent, to produce backcross progeny;

(d) selecting backcross progeny which may comprise QTL1 and optionally QTL2 for resistance to *Fusarium oxysporum* f. sp. *radicis-cucumerinum* and the other desired trait; and (e) optionally repeating steps c) and d) one or more times in succession to produce selected fourth or higher backcross progeny that may comprise the other desired trait and has resistance to *Fusarium oxysporum* f sp. *radicis-cucumerinum*. The invention includes a cucumber plant produced by this method and the cucumber fruit obtained therefrom.

Optionally selfing steps are performed after any of the crossing or backcrossing steps. Selection for a plant which may comprise the QTL1 and optionally QTL2 of the invention and the other desired trait can alternatively be done following any crossing or selfing step of the method.

The invention further provides a method for the production of a cucumber plant having resistance to *Fusarium oxysporum* f sp. *radicis-cucumerinum* as defined herein by using a doubled haploid generation technique to generate a doubled haploid line that homozygously may comprise the QTL1 and optionally QTL2 that leads to resistance to *Fusarium oxysporum* f sp. *radicis-cucumerinum*.

The invention also relates to a method for the production of a cucumber plant which may comprise QTL1 and optionally QTL2 that leads to resistance to *Fusarium oxysporum* f. sp. *radicis-cucumerinum*, by using a seed that may comprise QTL1 and optionally QTL2 in its genome that leads to resistance to *Fusarium oxysporum* f sp. *radicis-cucumerinum* for growing the said cucumber plant. The seeds are suitably seeds of which a representative sample was deposited with the NCIMB under deposit numbers NCIMB 42438 and NCIMB 42439.

The invention also relates to a method for seed production which may comprise growing cucumber plants from seeds of the invention, allowing the plants to produce seeds by allowing pollination to occur, and harvesting those seeds. Production of the seeds is suitably done by crossing or selfing. Preferably, the seeds so produced have the capability to grow into plants that have resistance to *Fusarium oxysporum* f. sp. *radicis-cucumerinum*.

In one embodiment, the invention relates to a method for the production of a cucumber plant having QTL1 and optionally QTL2 that leads to resistance to *Fusarium oxysporum* f. sp. *radicis-cucumerinum*, by using tissue culture of plant material that carries the QTL1 and optionally QTL2 in its genome.

The invention furthermore relates to a method for the production of a cucumber plant having the QTL1 and optionally QTL2 that leads to resistance to *Fusarium oxysporum* f sp. *radicis-cucumerinum*, by using vegetative reproduction of plant material that carries the QTL1 and optionally QTL2 in its genome.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Phenotyping of Resistance to *Fusarium oxysporum* f. Sp. *Radicis-Cucumerinum* (Forc)

Seeds of a parent line susceptible to Forc, a parent line resistant to Forc, and of an F1 between those two parents were sown in seedling trays filled with potting soil and kept in a climate chamber at 26° C. Of each accession sufficient plants to be able to get two repetitions of 12 plants were sown. At 6 days after sowing the seedlings were inoculated by the root dipping method. A few cm. are cut from the roots and the seedlings are subsequently dipped for at least 2 minutes in the prepared inoculum, using a suspension containing $5 \times 10^6$ spores/ml. The susceptible parent line had rather poor germination and only 11 plants could be used for the 2nd repetition.

Inoculated seedlings were subsequently transplanted in trays filled with moist soil, and further kept in the greenhouse at a temperature of 25° C. by day and night.

Scoring was started at 7 days after inoculation according to the features described in Table 1. The scores of the $2^{nd}$ repetition of 3 Apr. 2015 were not recorded (NA). Table 2 presents the scores of this bio-assay.

TABLE 2

Bio-assay scores *Fusarium oxysporum* f. sp. *radicis-cucumerinum* resistance

| | | Date | | | | | | | |
|---|---|---|---|---|---|---|---|---|---|
| | | 31 Mar. 2014 | | | | 3 Apr. 2015 | | | |
| | Rep. | cotyl 0/1/2/3 | leaves 0/1/2/3 | hypo rot N/Y | wilt N/Y | cotyl 0/1/2/3 | leaves 0/1/2/3 | hypo rot N/Y | wilt N/Y |
| Susc. | 1 | 8/4/0/0 | 12/0/0/0 | 11/1 | 3/9 | 1/4/5/2 | 0/12/0/0 | 1/11 | 2/10 |
| | 2 | 11/0/0/0 | 11/0/0/0 | 11/0 | 11/0 | NA | NA | NA | NA |
| Res. | 1 | 12/0/0/0 | 12/0/0/0 | 12/0 | 11/1 | 7/3/2/0 | 12/0/0/0 | 12/0 | 12/0 |
| | 2 | 12/0/0/0 | 12/0/0/0 | 12/0 | 11/1 | NA | NA | NA | NA |
| F1 Susc. × | 1 | 12/0/0/0 | 12/0/0/0 | 12/0 | 9/3 | 7/4/1/0 | 12/0/0/0 | 12/0 | 8/4 |
| Res. | 2 | 11/1/0/0 | 12/0/0/0 | 12/0 | 9/3 | NA | NA | NA | NA |

| | | Date | | | | | | | |
|---|---|---|---|---|---|---|---|---|---|
| | | 7 Apr. 2015 | | | | 13 Apr. 2015 | | | |
| | Rep. | cotyl 0/1/2/3 | leaves 0/1/2/3 | hypo rot N/Y | wilt N/Y | cotyl 0/1/2/3 | leaves 0/1/2/3 | hypo rot N/Y | wilt N/Y |
| Susc. | 1 | 0/1/0/11 | 1/0/1/10 | 0/12 | 1/11 | 0/0/0/12 | 0/0/0/12 | 0/12 | 0/12 |
| | 2 | 0/0/0/11 | 0/0/0/11 | 0/11 | 0/11 | 0/0/0/11 | 0/0/0/11 | 0/11 | 0/11 |
| Res. | 1 | 7/5/0/0 | 10/2/0/0 | 8/4 | 8/4 | 1/2/4/5 | 0/2/0/10 | 6/6 | 8/4 |
| | 2 | 8/3/1/0 | 10/1/0/1 | 11/1 | 9/3 | 0/0/0/12 | 2/1/3/6 | 5/7 | 8/4 |

TABLE 2-continued

Bio-assay scores Fusarium oxysporum f. sp. radicis-cucumerinum resistance

| F1 Susc. × | 1 | 9/3/0/0 | 12/0/0/0 | 8/4 | 10/2 | 1/0/0/11 | 4/1/0/7 | 2/10 | 5/7 |
| Res. | 2 | 4/6/2/0 | 11/1/0/0 | 5/7 | 5/7 | 0/0/0/12 | 0/1/1/10 | 2/10 | 4/8 |

For the cotyledons and leaves at each observation date the number of plants in the scoring categories 0, 1, 2, and 3 are given, whereby 0 means no symptoms, 1 means some yellowing, 2 is moderate to heavy yellowing, and 3 means the plant is dead.

For hypocotyl rot and wilting, at each observation date it is indicated whether plants show the symptom (Y) or not (N). A plant is scored with 'Y' for wilting when the whole plant is wilted, not just a few leaves.

At the first observation date the differences are not yet very large, but the susceptible parent line shows already quite some plants that are wilted. At the $2^{nd}$ observation date most plants of the susceptible parent line show hypocotyl rot and are completely wilted, and leaves start yellowing. The resistant parent line is still strong, and only shows some to moderate yellowing of the cotyledons. The intermediate or F1 line has some yellowing of the cotyledons and some wilted plants as well, but does not yet show hypocotyl rot.

The $3^{rd}$ observation, at about 2 weeks after inoculation, shows most plants of the susceptible parent line in category '3', and they have hypocotyl rot and wilting. The resistant parent line has some plants that are wilted or have hypocotyl rot, but well over 50% does not show these symptoms yet. In some plant also yellowing of cotyledons and leaves is observed. The F1 shows recovery of some initially wilted plants, indicating that these plants are clearly stronger than the susceptible parent. Yellowing of cotyledons and leaves is comparable to the resistant parent at this stage.

The final observation shows especially a difference between the resistant and the susceptible parent for hypocotyl rot and wilting, whereby part of the plants of the resistant parent line are still scoring 'N' for these features, while all susceptible plants score 'Y'. The intermediate or F1 plants are not as strong as the resistant parent, but still perform better than the susceptible parent.

The invention is further described by the following numbered paragraphs:

1. Cucumber plant which carries a QTL1 in its genome that leads to resistance to *Fusarium oxysporum* f. sp. *radicis-cucumerinum*, which QTL1 is located on chromosome 3 between marker sequences SEQ ID No. 1 and SEQ ID No. 2, whereby the 'G' on position 65 in SEQ ID No. 1 corresponds to the physical position 6,996,646 bp of the public cucumber genome and 'TC' on positions 74 and 75 in SEQ ID No. 2 correspond to the physical positions 9,480,131 and 9,480,132 bp of the public cucumber genome.

2. Cucumber plant of paragraph 1, wherein QTL1 is as comprised in the genome of a cucumber plant representative seed of which was deposited with the NCIMB under deposit numbers NCIMB 42438 and NCIMB 42439, and is in particular located therein between marker sequences SEQ ID No. 1 and SEQ ID No. 2.

3. Cucumber plant of paragraph 1 or 2, wherein the presence of QTL1 can be identified by any of the markers on chromosome 3 having SEQ ID No. 3, and/or SEQ ID No. 4.

4. Cucumber plant of any one of paragraphs 1-3, which further comprises a QTL2 which is located on chromosome 5 between marker sequences SEQ ID No. 5 and SEQ ID No. 6, whereby the 'T' on position 87 in SEQ ID No. 5 corresponds to the physical position 20,877,766 bp of the public cucumber genome and the 'A' on position 39 in SEQ ID No. 6 corresponds to the physical position 23,250,404 bp of the public cucumber genome.

5. Cucumber plant of paragraph 4, wherein QTL2 is as comprised in the genome of a cucumber plant representative seed of which was deposited with the NCIMB under deposit number NCIMB 42439, and is in particular located therein between marker sequences SEQ ID No. 5 and SEQ ID No. 6.

6. Cucumber plant of paragraph 4 or 5, wherein the presence of QTL2 can be identified by any of the markers on chromosome 5 having SEQ ID No. 7, SEQ ID No. 8, SEQ ID No. 9, and/or SEQ ID No. 10, or any combination of these SEQ ID Nos.

7. Cucumber plant of any one of paragraphs 1-6, comprising QTL1 in heterozygous form; or comprising QTL1 in homozygous form, or comprising QTL1 and QTL2 in heterozygous form, or comprising QTL1 in homozygous form and QTL2 in heterozygous form, or comprising QTL2 in homozygous form and QTL1 in heterozygous form, or comprising both QTL1 and QTL2 in homozygous form, whereby preferably QTL1 is present in homozygous form, which plant is resistant to *Fusarium oxysporum* f sp. *radicis-cucumerinum*.

8. Cucumber plant of any one of paragraphs 1-7, which cucumber plant is resistant to *Fusarium oxysporum* f. sp. *radicis-cucumerinum*.

9. Cucumber plant of any one of paragraphs 1-8, obtainable by crossing a cucumber plant that does not show resistance to *Fusarium oxysporum* f. sp. *radicis-cucumerinum* with a cucumber plant representative seed of which was deposited with the NCIMB under deposit numbers NCIMB 42438 or NCIMB 42439, optionally selfing the progeny from the cross and selecting in the F1 and/or the F2 for plants showing resistance to *Fusarium oxysporum* f. sp. *radicis-cucumerinum* and/or comprising a marker of SEQ ID No. 3, and/or SEQ ID No. 4.

10. Cucumber plant of paragraph 9 wherein in the F1 and/or F2 plants are selected that further comprise a marker of SEQ ID No. 7, SEQ ID No. 8, SEQ ID No. 9, and/or SEQ ID No. 10.

11. Propagation material suitable for producing a plant of any one of paragraphs 1-10, wherein the propagation material is suitable for sexual reproduction, and is in particular selected from microspores, pollen, ovaries, ovules, embryo sacs and egg cells, or is suitable for vegetative reproduction, and is in particular selected from cuttings, roots, stems, cells, protoplasts, or is suitable for tissue cultures of regenerable cells, and is in particular selected from leaves, pollen, embryos, cotyledon, hypocotyls, meristematic cells, roots, root tips, anthers, flowers, seeds and stems, wherein the plant produced from the propagation material comprises QTL1 and optionally QTL2 that leads to resistance to *Fusarium oxysporum* f sp. *radicis-cucumerinum*.

12. Marker for identification of QTL1 which when present in the genome of a cucumber plant leads to resistance to *Fusarium oxysporum* f. sp. *radicis-cucumerinum*, which marker is selected from the group of SEQ ID No. 1, SEQ ID No. 2, SEQ ID No. 3, and SEQ ID No. 4.

13. Marker for identification of QTL2 which when present in the genome of a cucumber plant in combination with QTL1 leads to resistance to *Fusarium oxysporum* f sp. *radicis-cucumerinum*, which marker is selected from the group of SEQ ID No. 5, SEQ ID No. 6, SEQ ID No. 7, SEQ ID No. 8, SEQ ID No. 9, and SEQ ID No. 10.

14. Use of a marker for identification of QTL1 which when present in the genome of a cucumber plant leads to resistance to *Fusarium oxysporum* f. sp. *radicis-cucumerinum*, which marker is selected from the group of SEQ ID No. 1, SEQ ID No. 2, SEQ ID No. 3, and SEQ ID No. 4.

15. Use of a marker for identification of QTL2 which when present in the genome of a cucumber plant in combination with QTL1 leads to resistance to *Fusarium oxysporum* f sp. *radicis-cucumerinum*, which marker is selected from the group of SEQ ID No. 5, SEQ ID No. 6, SEQ ID No. 7, SEQ ID No. 8, SEQ ID No. 9, and SEQ ID No. 10.

---

What is claimed is:

1. A cucumber plant comprising QTL1 in its genome that leads to resistance to *Fusarium oxysporum* f. sp. *radicis-cucumerinum*,
wherein QTL1 is located on chromosome 3 between marker sequences SEQ ID No. 1 and SEQ ID No. 2, whereby the 'G' on position 65 in SEQ ID No. 1 corresponds to the physical position 6,996,646 bp of the public cucumber genome and 'TC' on positions 74 and 75 in SEQ ID No. 2 correspond to the physical positions 9,480,131 and 9,480,132 bp of the public cucumber genome,
wherein QTL1 is as comprised in the genome of a cucumber plant representative seed of which was deposited with the NCIMB under deposit numbers NCIMB 42438 and NCIMB 42439.

2. The cucumber plant as claimed in claim 1, wherein the presence of QTL1 is identified by a marker on chromosome 3 having SEQ ID No. 3, and/or SEQ ID No. 4.

3. The cucumber plant as claimed in claim 1, comprising QTL2
wherein QTL2 is located on chromosome 5 between marker sequences SEQ ID No. 5 and SEQ ID No. 6, whereby the 'T' on position 87 in SEQ ID No. 5 corresponds to the physical position 20,877,766 bp of the public cucumber genome and the 'A' on position 39 in SEQ ID No. 6 corresponds to the physical position 23,250,404 bp of the public cucumber genome,
wherein QTL2 is as comprised in the genome of a cucumber plant representative seed of which was deposited with the NCIMB under deposit number NCIMB 42439.

4. The cucumber plant as claimed in claim 3, wherein the presence of QTL2 is identified by a marker on chromosome 5 having SEQ ID No. 7, SEQ ID No. 8, SEQ ID No. 9, and/or SEQ ID No. 10.

5. The cucumber plant as claimed in claim 1, comprising QTL1 in heterozygous form; or comprising QTL1 in homozygous form, or comprising QTL1 and QTL2 in heterozygous form, or comprising QTL1 in homozygous form and QTL2 in heterozygous form, or comprising QTL2 in homozygous form and QTL1 in heterozygous form, or comprising both QTL1 and QTL2 in homozygous form, which plant is resistant to *Fusarium oxysporum* f. sp. *radicis-cucumerinum*.

6. The cucumber plant as claimed in claim 1, which cucumber plant is resistant to *Fusarium oxysporum* f sp. *radicis-cucumerinum*.

7. The cucumber plant as claimed in claim 1, obtainable by crossing a cucumber plant that does not show resistance to *Fusarium oxysporum* f sp. *radicis-cucumerinum* with a cucumber plant representative seed of which was deposited with the NCIMB under deposit numbers NCIMB 42438 or NCIMB 42439, optionally selfing the progeny from the cross and selecting in the F1 and/or the F2 for plants showing resistance to *Fusarium oxysporum* f. sp. *radicis-cucumerinum* and/or comprising a marker of SEQ ID No. 3, and/or SEQ ID No. 4.

8. The cucumber plant as claimed in claim 7 wherein in the F1 and/or F2 plants are selected that further comprise a marker of SEQ ID No. 7, SEQ ID No. 8, SEQ ID No. 9, and/or SEQ ID No. 10.

9. A propagation material suitable for producing the plant as claimed in claim 1, wherein the propagation material is suitable for sexual reproduction,
wherein the plant produced from the propagation material comprises QTL1 and optionally QTL2 that leads to resistance to *Fusarium oxysporum* f sp. *radicis-cucumerinum*.

10. A method for identifying QTL1 which when present in the genome of a cucumber plant leads to resistance to *Fusarium oxysporum* f. sp. *radicis-cucumerinum* comprising
determining the presence of a marker in the genome, which marker is selected from the group of SEQ ID No. 1, SEQ ID No. 2, SEQ ID No. 3, and SEQ ID No. 4,
wherein QTL1 is as comprised in the genome of a cucumber plant representative seed of which was deposited with the NCIMB under deposit numbers NCIMB 42438 and NCIMB 42439.

11. A method for identifying QTL2 which when present in the genome of a cucumber plant in combination with QTL1 leads to resistance to *Fusarium oxysporum* f. sp. *radicis-cucumerinum*, comprising
determining the presence of a marker in the genome, which marker is selected from the group of SEQ ID No. 5, SEQ ID No. 6, SEQ ID No. 7, SEQ ID No. 8, SEQ ID No. 9, and SEQ ID No. 10,
wherein QTL2 is as comprised in the genome of a cucumber plant representative seed of which was deposited with the NCIMB under deposit number NCIMB 42439.

12. The cucumber plant of claim 5, wherein QTL1 is present in homozygous form.

13. The propagation material of claim 9, wherein the propagation material is selected from microspores, pollen, ovaries, ovules, embryo sacs and egg cells, or is suitable for vegetative reproduction.

14. The propagation material of claim 9, wherein the propagation material is selected from cuttings, roots, stems, cells, protoplasts, or is suitable for tissue cultures of regenerable cells.

15. The propagation material of claim 9, wherein the propagation material is selected from leaves, pollen, embryos, cotyledon, hypocotyls, meristematic cells, roots, root tips, anthers, flowers, seeds and stems.

* * * * *

UNITED STATES PATENT AND TRADEMARK OFFICE
CERTIFICATE OF CORRECTION

PATENT NO. : 10,952,385 B2
APPLICATION NO. : 15/837149
DATED : March 23, 2021
INVENTOR(S) : Cornelis Haaring et al.

It is certified that error appears in the above-identified patent and that said Letters Patent is hereby corrected as shown below:

In the Claims

Claim 6 should read as follows:
6. The cucumber plant as claimed in claim 1, which cucumber plant is resistant to Fusarium oxysporum f. sp. radicis-cucumerinum.

Claim 7 should read as follows:
7. The cucumber plant as claimed in claim 1, obtainable by crossing a cucumber plant that does not show resistance to Fusarium oxysporum f. sp. radicis-cucumerinum with a cucumber plant representative seed of which was deposited with the NCIMB under deposit numbers NCIMB 42438 or NCIMB 42439, optionally selfing the progeny from the cross and selecting in the F1 and/or the F2 for plants showing resistance to Fusarium oxysporum f. sp. radicis-cucumerinum and/or comprising a marker of SEQ ID No. 3, and/or SEQ ID No. 4.

Claim 9 should read as follows:
9. A propagation material suitable for producing the plant as claimed in claim 1, wherein the propagation material is suitable for sexual reproduction, wherein the plant produced from the propagation material comprises QTL1 and optionally QTL2 that leads to resistance to Fusarium oxysporum f. sp. radicis-cucumerinum.

Signed and Sealed this
Twenty-third Day of August, 2022

Katherine Kelly Vidal
*Director of the United States Patent and Trademark Office*